US012778559B2

(12) United States Patent
Ji et al.

(10) Patent No.: US 12,778,559 B2
(45) Date of Patent: Nov. 3, 2026

(54) MEDICAL IMAGING SYSTEM, CONTROL METHOD THEREFOR, AND NON-TRANSITORY COMPUTER-READABLE MEDIUM

(71) Applicant: GE Precision Healthcare LLC, Waukesha, WI (US)

(72) Inventors: Wei Ji, Wuxi (CN); Weijie Zhang, Wuxi (CN); Hui Ning, Wuxi (CN); Zhiwen Wang, Wuxi (CN); Youli Sun, Wuxi (CN)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 19/085,867

(22) Filed: Mar. 20, 2025

(65) Prior Publication Data

US 2025/0295395 A1 Sep. 25, 2025

(30) Foreign Application Priority Data

Mar. 21, 2024 (CN) ......................... 202410329993.0

(51) Int. Cl.
*A61B 5/05* (2021.01)
*A61B 8/00* (2006.01)

(52) U.S. Cl.
CPC ............. *A61B 8/54* (2013.01); *A61B 8/4444* (2013.01); *A61B 8/461* (2013.01); *A61B 8/58* (2013.01)

(58) Field of Classification Search
CPC .. A61B 8/54; A61B 8/58; A61B 8/461; A61B 8/4444
See application file for complete search history.

(56) References Cited

U.S. PATENT DOCUMENTS

| | | | | |
|---|---|---|---|---|
| 6,678,626 B2 | 1/2004 | Fallon | | |
| 10,092,274 B2 | 10/2018 | Hopple | | |
| 10,709,427 B2 | 7/2020 | Markoff | | |
| 11,717,260 B2 | 8/2023 | Iwahashi | | |
| 11,730,455 B2 | 8/2023 | Cao | | |
| 2019/0019317 A1* | 1/2019 | Zhang | .................... | A61B 6/582 |
| 2022/0114801 A1* | 4/2022 | Xu | ......................... | G06V 10/44 |
| 2022/0413171 A1* | 12/2022 | Berent | ...................... | G01T 1/17 |

FOREIGN PATENT DOCUMENTS

CN 107328866 B 10/2019

OTHER PUBLICATIONS

Lorentsson et al., "Method for automatic detection of defective ultrasound linear array transducers based on uniformity assessment of clinical images—A case study," J Appl Clin Med Phys. Jan. 11, 2018;19(2):265-274. doi: 10.1002/acm2.12248, 10 pages.

* cited by examiner

*Primary Examiner* — Joel F Brutus
(74) *Attorney, Agent, or Firm* — SPQ IP LLC

(57) ABSTRACT

A medical imaging system including a scanning device, configured to scan an object to be tested, to obtain imaging data containing information about the object to be tested, wherein the scanning device has a front end portion for transmitting a signal to and receiving a signal from the object to be tested. The control method includes: detecting, according to data obtained by the scanning device by scanning a predetermined object to be tested, a type of a fault that has occurred in the front end portion of the scanning device. The present application can improve the stability of the medical imaging system and shorten the waiting time of hospitals and patients.

20 Claims, 7 Drawing Sheets

MEDICAL IMAGING SYSTEM, CONTROL METHOD THEREFOR, AND NON-TRANSITORY COMPUTER-READABLE MEDIUM

CROSS-REFERENCE TO RELATED APPLICATION

This application claim priority to Chinese Patent Application No. 202410329993.0, which was file on Mar. 21, 2024 at the Chinese Patent Office. The entire contents of the above-listed application are incorporated by reference herein in their entirety.

TECHNICAL FIELD

Embodiments of the present application relate to the technical field of medical devices, in particular to a medical imaging system, a control method therefor, and a non-transitory computer-readable medium.

BACKGROUND

Medical imaging devices can non-invasively obtain internal tissue images of an object to be imaged. For example, a scanning device of the medical imaging device may scan a predetermined site of the object to be imaged to obtain imaging data including information about the predetermined site.

Common medical imaging devices are, for example, ultrasound imaging systems, magnetic resonance imaging (MRI) systems, computed tomography (CT) scanning systems, etc.

It should be noted that the above introduction of the background is only for the convenience of clearly and completely describing the technical solutions of the present application, and for the convenience of understanding for those skilled in the art.

SUMMARY

When a medical imaging device is damaged or cannot operate normally, an operator usually needs to wait for a professional to repair the device. The waiting process described above generally takes a long time, which causes great inconvenience to hospitals and patients. In general, it is inevitable that the device cannot be used during the waiting process described above, because the operator of the medical imaging device does not have the qualifications for detecting and repairing damage.

To resolve at least one technical problem described above or a similar technical problem, embodiments of the present application provide a medical imaging system, a control method therefor, and a non-transitory computer-readable medium. In the control method for the medical imaging system, a type of a fault that has occurred in a front end portion of a scanning device is detected according to data obtained by the scanning device by scanning a predetermined object to be tested. The inventors have realized that front end portions of medical imaging devices usually have a plurality of imaging channels, which, to a certain extent, provides the possibility for the medical imaging device to temporarily operate by bypassing the fault itself. Specifically, after fault detection is performed on the front end portion comprising the plurality of imaging channels by using an implementation of the present application, a faulty channel among the plurality of channels may be subsequently processed (e.g., shielded, etc.) according to a detection result, while the operating state of a normal channel is maintained. Based on this, the availability of the medical imaging system can be determined according to the type of the fault. Therefore, the medical imaging system is appropriately used while waiting for the medical imaging system to be repaired, so as to improve the stability of the medical imaging system and shorten the waiting time of hospitals and patients.

According to one aspect of the embodiments of the present application, a control method for a medical imaging system is provided. The medical imaging system comprises:

- a scanning device, configured to scan an object to be tested, to obtain imaging data containing information about the object to be tested, wherein the scanning device has a front end portion for transmitting a signal to and receiving a signal from the object to be tested.

The control method comprises:

- detecting, according to data obtained by the scanning device by scanning a predetermined object to be tested, a type of a fault that has occurred in the front end portion of the scanning device.

According to another aspect of the embodiments of the present application, a medical imaging system is provided. The medical imaging system comprises:

- a scanning device, configured to scan an object to be tested, to obtain imaging data containing information about the object to be tested, wherein the scanning device has a front end portion for transmitting a signal to and receiving a signal from the object to be tested; and
- a control apparatus, the control apparatus detecting, according to data obtained by the scanning device by scanning a predetermined object to be tested, a type of a fault that has occurred in the front end portion of the scanning device.

According to still another aspect of the embodiments of the present application, a non-transitory computer-readable medium is provided. The non-transitory computer-readable medium has a computer program stored therein, wherein the computer program has at least one code segment, the at least one code segment being executable by a machine to cause the machine to perform the steps of the method as described in the above embodiments.

One of the beneficial effects of the embodiments of the present application is that: In the control method for the medical imaging system, the type of the fault that has occurred in the front end portion of the scanning device is detected according to the data obtained by the scanning device by scanning the predetermined object to be tested. In the embodiments, the front end portion is selected as a fault detection subject, and considering that the front end portion usually has a plurality of imaging channels, when an imaging channel is damaged less seriously, the front end portion still has the possibility of operating. By using the method provided in the embodiments of the present application, the availability of the medical imaging system can be determined according to the type of the fault. Therefore, the medical imaging system is appropriately used while waiting for the medical imaging system to be repaired, so as to improve the stability of the medical imaging system and shorten the waiting time of hospitals and patients.

With reference to the following description and drawings, specific implementations of the embodiments of the present application are disclosed in detail, and the way in which the principles of the embodiments of the present application can be employed are illustrated. It should be understood that the embodiments of the present application are not limited in scope thereby. Within the scope of the spirit and clauses of the appended claims, the embodiments of the present application comprise many changes, modifications, and equivalents.

BRIEF DESCRIPTION OF THE DRAWINGS

The included drawings are used to provide further understanding of the embodiments of the present application, which constitute a part of the description and are used to illustrate the implementations of the present application and explain the principles of the present application together with textual description. Evidently, the drawings in the following description are merely some embodiments of the present application, and those of ordinary skill in the art may obtain other implementations according to the drawings without involving inventive effort. In the drawings.

DETAILED DESCRIPTION

The foregoing and other features of the embodiments of the present application will become apparent from the following description with reference to the drawings. In the description and drawings, specific implementations of the present application are disclosed in detail, and part of the implementations in which the principles of the embodiments of the present application may be employed are indicated. It should be understood that the present application is not limited to the described implementations. On the contrary, the embodiments of the present application include all modifications, variations, and equivalents which fall within the scope of the appended claims.

In the embodiments of the present application, the terms "first", "second", etc. are used to distinguish between different elements in terms of appellation, but do not represent a spatial arrangement, a temporal order, or the like of these elements, and these elements should not be limited by these terms. The term "and/or" includes any one of and all combinations of one or more associated listed terms. The terms "comprise", "include", "have", etc., refer to the presence of described features, elements, components, or assemblies, but do not exclude the qpresence or addition of one or more other features, elements, components, or assemblies. The terms "pixel" and "voxel" may be used interchangeably.

In the embodiments of the present application, the singular forms "a", "the", etc., include plural forms, and should be broadly construed as "a type of" or "a class of" rather than being limited to the meaning of "one". Furthermore, the term "the" should be construed as including both the singular and plural forms, unless otherwise specified in the context. In addition, the term "according to" should be construed as "at least in part according to . . . " and the term "based on" should be construed as "based at least in part on . . . ", unless otherwise specified in the context.

The features described and/or illustrated for one embodiment may be used in one or more other embodiments in an identical or similar manner, combined with features in other embodiments, or replace features in other embodiments. The term "include/comprise" when used herein refers to the presence of features, integrated components, steps, or assemblies, but does not exclude the presence or addition of one or more other features, integrated components, steps, or assemblies.

Some embodiments of the present application provide a control method for a medical imaging system.

Figure 1:
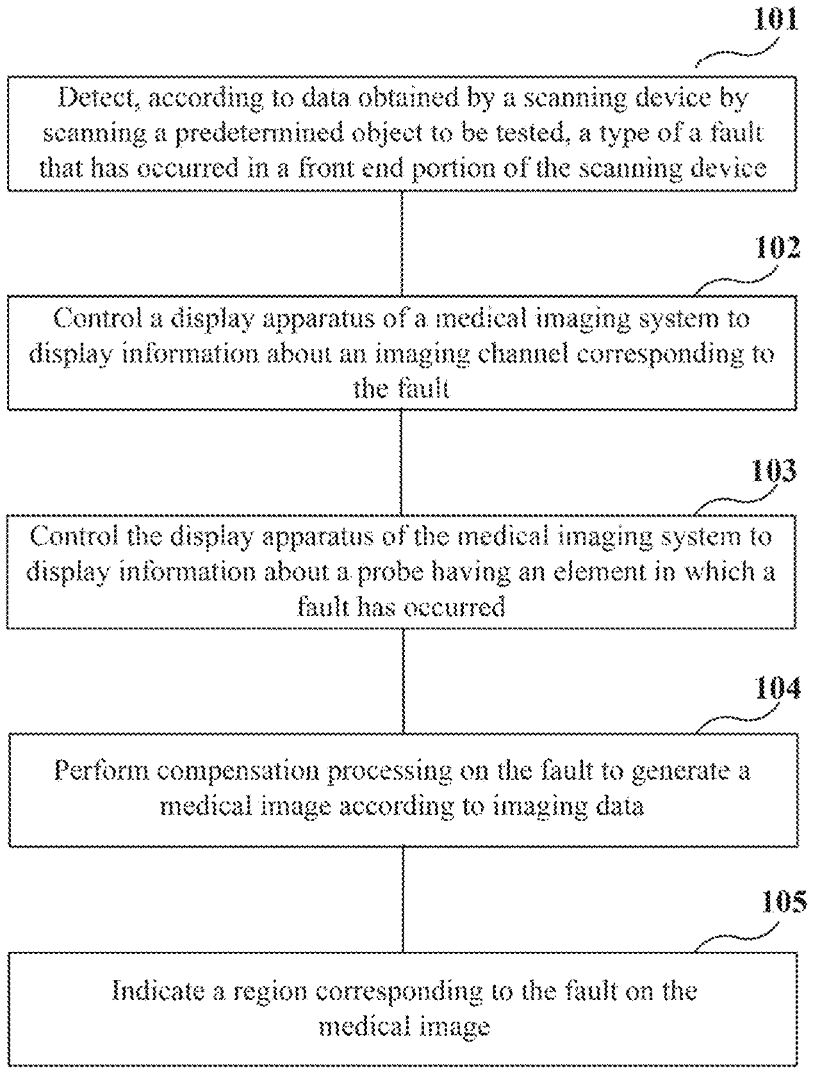
FIG. 1 is a schematic diagram of a control method for a medical imaging system according to some embodiments of the present application.

FIG. 1 is a schematic diagram of a control method for a medical imaging system according to some embodiments of the present application. A scanning device of the medical imaging system is configured to scan an object to be tested, to obtain imaging data containing information about the object to be tested, wherein the scanning device has a front end portion for transmitting a signal to and receiving a signal from the object to be tested. As shown in FIG. 1, the control method for the medical imaging system includes:

operation 101: detecting, according to data obtained by a scanning device by scanning a predetermined object to be tested, a type of a fault that has occurred in a front end portion of the scanning device.

The control method may be implemented by means of an algorithm by a control apparatus, e.g., a processor of the medical imaging system. By means of the control method described above, the availability of the medical imaging system can be determined according to the type of the fault. Therefore, the medical imaging system is appropriately used while waiting for the medical imaging system to be repaired, so as to improve stability of the medical imaging system. Specifically, a front end portion of the medical imaging system usually includes a plurality of imaging channels (described in exemplary detail below), and each or several of the plurality of imaging channels each contain a component that is independent of the other channels. In this way, when components in some of the channels are damaged, there is still the possibility of temporarily performing a medical imaging function by using the remaining channels. The control method described above in the present application then determines, by means of detecting the type of the fault of the front end portion, the possibility of temporarily performing the imaging function. Embodiments of the present application can improve the availability of the medical imaging system compared with a conventional method in which an operator can only wait for repair in case of any fault.

In the following descriptions of the present application, the medical imaging system being an ultrasound imaging system is used as an example for description, but the content of these descriptions is not limited to the ultrasound imaging system and can also be applied to other types of medical imaging systems.

Figure 2:
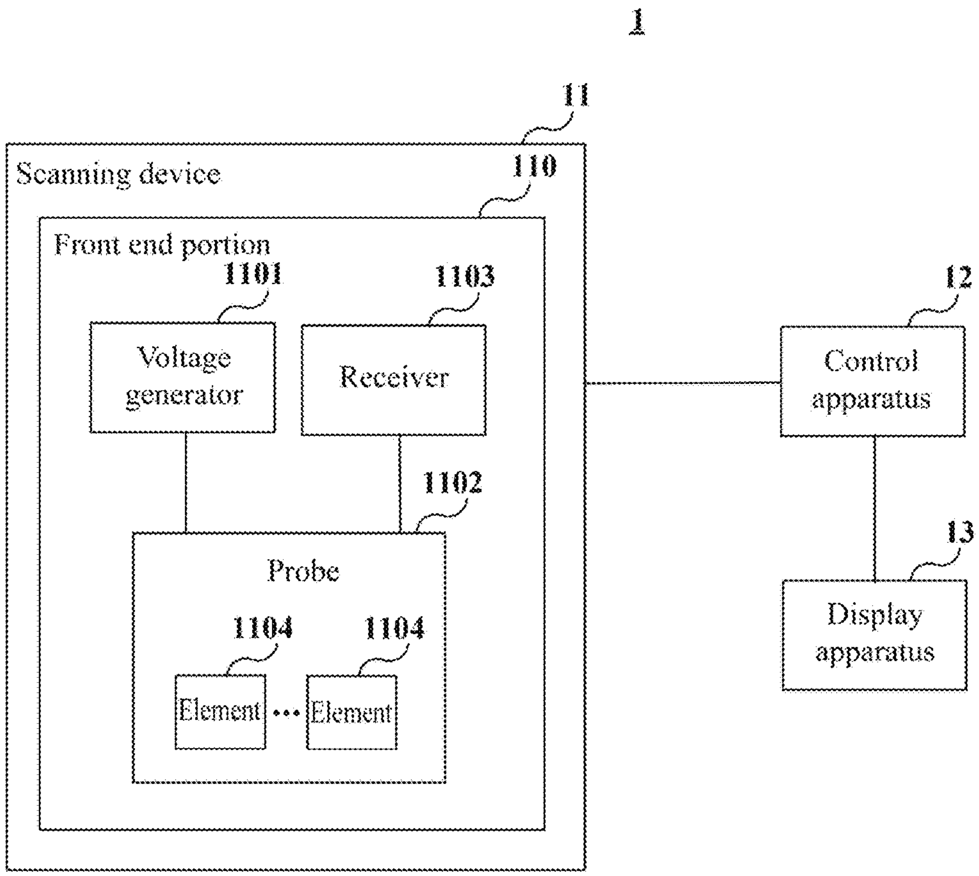
FIG. 2 is a schematic diagram of an ultrasound imaging system.

FIG. 2 is a schematic diagram of an ultrasound imaging system. As shown in FIG. 2, a medical imaging system 1 as an ultrasound imaging system includes a scanning device 11 and a control apparatus 12. The scanning device 11 has a front end portion 110. The front end portion 110 can transmit a signal (e.g., the signal may be an ultrasound wave) to a site to be imaged (i.e., an object to be tested) of an object to be imaged, and the front end portion 110 can also receive a signal (e.g., the returned signal may be an echo of an ultrasound wave) returned from the site to be imaged (i.e., the object to be tested), thereby obtaining imaging data. The imaging data may be used to generate a medical image, and the medical image currently scanned and acquired refers to a medical image (e.g., an anatomical image of a particular slice, etc.) that may reflect the state (e.g., morphology) at a current time (i.e., real-time) of an imaged site (e.g., organs or tissues such as a blood vessel and the heart) of the object to be imaged.

In addition, as shown in FIG. 2, the medical imaging system 1 may further include a display apparatus 13. The display apparatus 13 may display a medical image. Furthermore, the display apparatus 13 may also display a user interface (UI).

As shown in FIG. 2, the front end portion 110 may include: a voltage generator 1101, a probe 1102, and a receiver 1103.

The voltage generator 1101 may generate a pulse voltage, for example, the voltage generator 1101 may be a pulser chip.

The probe 1102 may have a plurality of elements 1104, the elements 1104 may transmit signals under the driving of the pulse voltage generated by the voltage generator 1101 or the elements 1104 may receive signals, and the signals received by the elements 1104 may be transmitted to the receiver 1103.

Each element 1104 may include a piezoelectric material (e.g., piezoelectric ceramic), whereby: an element 1104 configured to emit an ultrasound wave may generate mechanical vibration when receiving the pulse voltage generated by the voltage generator 1101, thereby emitting an ultrasound wave. In addition, an element 1104 configured to receive an echo of an ultrasound wave can generate a corresponding electrical signal (e.g., a voltage signal) when receiving an ultrasound wave.

The receiver 1103 can process an electrical signal corresponding to a signal received by the element 1104. For example, the receiver 1103 may be an analog front end chip, and the analog front end chip can perform processing such as sampling, filtering, and amplification on electrical signals.

The front end portion 110 may have N imaging channels, and the N imaging channels may be divided into M groups, each group including n imaging channels, wherein both N and n are natural numbers and n is less than or equal to N.

The front end portion 110 includes a plurality of voltage generators 1101, the quantity of voltage generators 1101 is the same as the quantity of groups of the imaging channels, and each group corresponds to one voltage generator 1101. The front end portion 110 includes a plurality of receivers 1103, the quantity of receivers 1103 is the same as the quantity of groups of the imaging channels, and each group corresponds to one receiver 1103.

In the present application, the medical imaging system 1 may be equipped with one or more probes 1102. When medical imaging scanning is performed, one of the probes 1102 is activated, and then the activated probe 1102 is connected to the front end portion 110 to perform transmission and reception of signals.

A plurality of elements 1104 of each probe 1102 may be divided into a plurality of groups, and each group includes at least one element 1104. In each probe 1102, the quantity of groups of the elements 1104 may be the same as the quantity of imaging channels or the quantity of groups of the imaging channels, and each group of elements 1104 may correspond to each imaging channel or each group of imaging channels.

Different imaging channels or different groups of imaging channels of the front end portion 110 may correspond to different regions of a medical image, that is, imaging data corresponding to each imaging channel or each group of imaging channels may be used to generate a complete medical image, and the medical image may be displayed on the display apparatus 13. For example, the imaging data corresponding to each imaging channel or each group of imaging channels may be assigned a specific weight value, and the control apparatus 12 may generate a complete medical image according to the imaging data corresponding to each imaging channel or each group of imaging channels and the weight value of the imaging data.

The following description of the present application may be based on the following example:

- The quantity N of imaging channels of the front end portion 110 is equal to 128, wherein numbers of the imaging channels may be from 0 to 127;
- starting from the imaging channel numbered 0, every n=16 imaging channels form a group, the quantity M of groups of the imaging channels is equal to 8, and numbers of the groups are from 0 to 7;
- the front end portion 110 has eight voltage generators 1101, and each voltage generator 1101 corresponds to one group of imaging channels;
- the probe 1102 may have a plurality of elements 1104, and each element 1104 may correspond to one imaging channel; and
- the front end portion 110 has eight receivers 1103, and each receiver 1103 corresponds to one group of imaging channels.

In operation 101 of the present application, the control apparatus 12 may detect, according to data obtained by the scanning device 11 by scanning a predetermined object to be tested, a type of a fault that has occurred in the front end portion 110 of the scanning device 11. The predetermined object to be tested may be air.

In some examples, the scanning device 11 scans the predetermined object to be tested (e.g., air) to obtain first data; and in operation 101, the control apparatus 12 performs at least one of frequency spectrum analysis and energy pulse analysis on the first data, and determines, according to a result of the analysis, a type of a fault that has occurred in the front end portion 110 of the scanning device 11.

For example, the control apparatus 12 may perform frequency spectrum analysis on the first data to obtain a frequency spectrum of each imaging channel.

For another example, the control apparatus 12 may integrate frequency spectra of all the imaging channels of the front end portion 110 on the basis of the frequency spectrum analysis, to obtain an energy pulse analysis result.

The control apparatus 12 may determine, based on at least one of the result of the frequency spectrum analysis and the result of the energy pulse analysis, the type of the fault that has occurred in the front end portion 110.

The type of the fault that has occurred in the front end portion 110 may include at least one of the following faults:

a fault that has occurred in the voltage generator 1101, for example, a fault that has occurred in one or more voltage generators 1101;

a fault that has occurred in at least one element 1104 of the probe 1102;

a fault that has occurred in the receiver 1103, for example, a fault that has occurred in one or more receivers 1103; and interference to the front end portion 110 caused by an external signal.

The following describes, with reference to the drawings, a method for determining, by the control apparatus 12, the type of the fault that has occurred in the front end portion 110.

Figure 3:
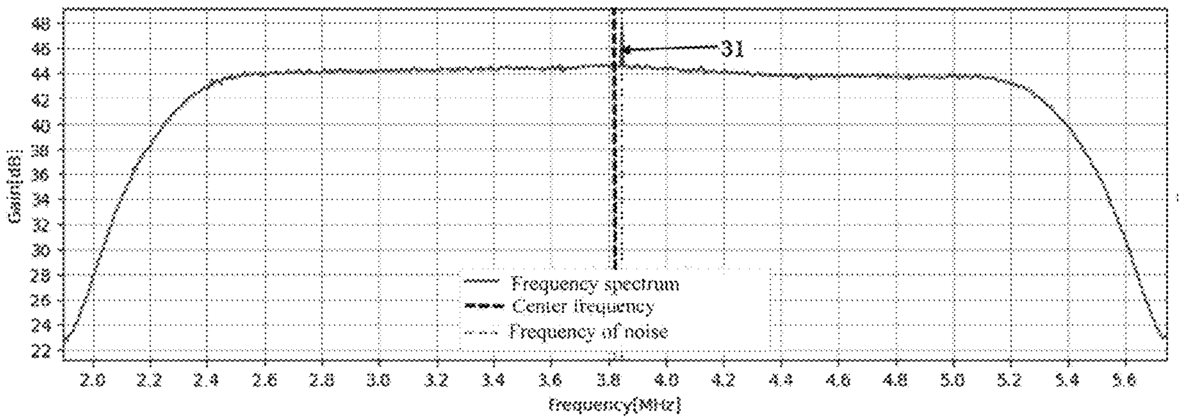
FIG. 3 is a schematic diagram of a frequency spectrum of an imaging channel obtained by a control apparatus 12 by performing frequency spectrum analysis on first data.

FIG. 3 is a schematic diagram of a frequency spectrum of an imaging channel obtained by a control apparatus 12 by performing frequency spectrum analysis on first data. FIG. 3 shows a frequency spectrum of a normal imaging channel.

In FIG. 3, the vertical axis represents a signal gain of the imaging channel in decibels (dB), and the horizontal axis represents the frequency of a signal of the imaging channel in megahertz (MHz). In FIG. 3, the center frequency of the signal of the imaging channel is about 3.823 MHz. A peak 31 represents noise, and the frequency of the noise is about 3.846 MHz.

In the present application, the control apparatus 12 may also integrate the frequency spectra of all the imaging channels of the front end portion 110, to obtain the energy pulse analysis result.

Figure 4:
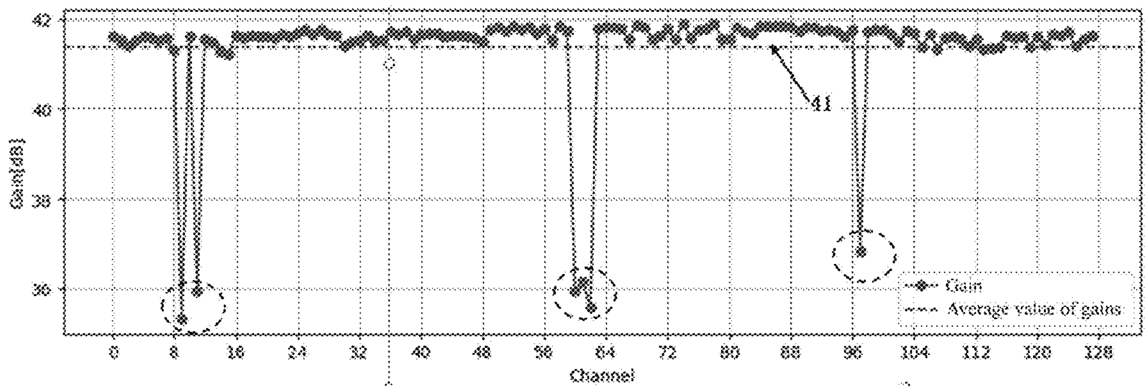
FIG. 4 is a schematic diagram of performing energy pulse analysis on first data by a control apparatus 12 to obtain an energy pulse analysis result.

FIG. 4 is a schematic diagram of performing energy pulse analysis on first data by a control apparatus 12 to obtain an energy pulse analysis result.

In FIG. 4, the vertical axis represents a signal gain in decibels (dB), and the horizontal axis represents identification information (e.g., a number) of each imaging channel of the front end portion 110, for example, the numbers of the imaging channels are from 0 to 127. A dashed line 41 represents the average value of gains of all imaging channels of the front end portion 110. The gains of imaging channels shown by dashed line circles are obviously lower than the average value. In FIG. 4, for each imaging channel, a gain of the imaging channel at a center frequency may be used as the gain of the imaging channel.

In the present application, if the difference between the gain of one imaging channel and the average value of the gains of all the imaging channels of the front end portion 110 is greater than a first threshold, the control apparatus 12 determines that this imaging channel corresponds to a fault. In addition, if imaging channels corresponding to a fault are scattered (e.g., the imaging channels corresponding to the fault are not continuous, or the quantity of continuous imaging channels is less than a second threshold), the control apparatus 12 determines that a fault has occurred in at least one element 1104 of the probe 1102. Therefore, in the example shown in FIG. 4, the control apparatus 12 determines that a fault has occurred in the element 1104 corresponding to the imaging channels numbered 09, 60, 61, and 98 in the probe 1102.

Figure 5:
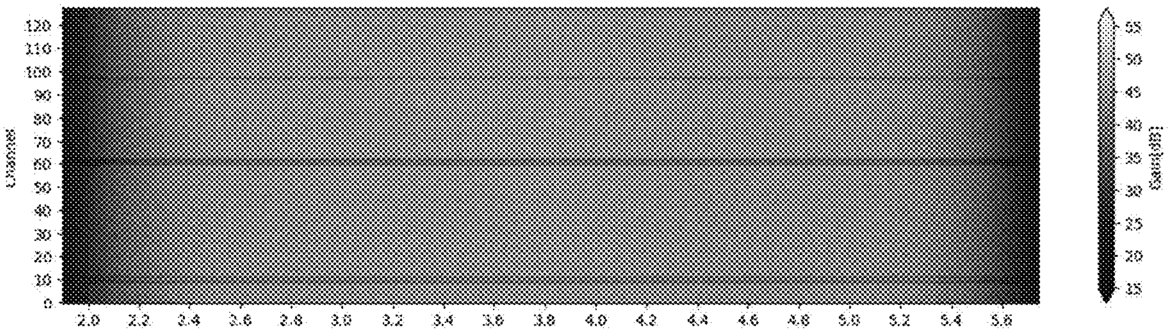
FIG. 5 is a schematic diagram of another representation of an energy pulse analysis result.

FIG. 5 is a schematic diagram of another representation of an energy pulse analysis result.

In FIG. 5, the vertical axis represents identification information (e.g., a number) of each imaging channel of the front end portion 110, for example, the numbers of the imaging channels are from 0 to 127. The horizontal axis represents the frequency of a signal of each imaging channel in megahertz (MHz). Different grayscales or colors represent signal gains in decibels (dB).

FIG. 5 corresponds to FIG. 4, and in FIG. 5, signal gains of the imaging channels numbered 09, 60, 61, and 98 at each frequency are obviously lower than those of the other channels. Therefore, the control apparatus 12 determines that a fault has occurred in the element 1104 corresponding to the imaging channels numbered 09, 60, 61, and 98 in the probe 1102.

Figure 6:
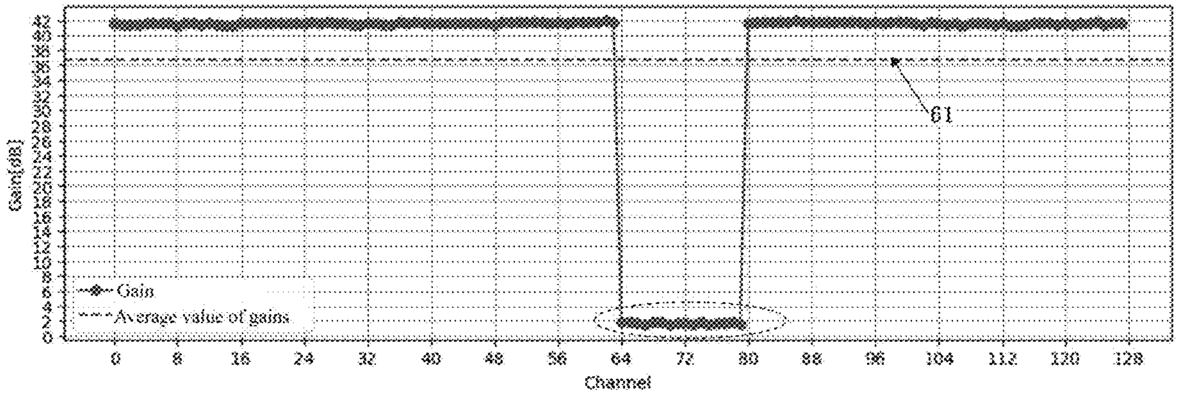
FIG. 6 is another schematic diagram of performing energy pulse analysis on first data by a control apparatus 12 to obtain an energy pulse analysis result.

FIG. 6 is another schematic diagram of performing energy pulse analysis on first data by a control apparatus 12 to obtain an energy pulse analysis result.

In FIG. 6, a dashed line 61 represents the average value of gains of all imaging channels of the front end portion 110. The gains of imaging channels shown by a dashed line circle are obviously lower than the average value. In FIG. 6, for each imaging channel, a gain of the imaging channel at the center frequency may be used as the gain of the imaging channel.

In the present application, if the difference between the gain of one imaging channel and the average value of the gains of all the imaging channels of the front end portion 110 is greater than the first threshold, the control apparatus 12 determines that this imaging channel corresponds to a fault. In addition, if imaging channels corresponding to a fault are continuous (e.g., the numbers of the imaging channels corresponding to the fault are continuous, and the quantity of the continuous numbers is greater than a third threshold), the control apparatus 12 determines that a fault has occurred in at least one voltage generator 1101 or receiver 1103 of the front end portion 110. Therefore, in the example shown in FIG. 6, the control apparatus 12 determines that a fault has occurred in the voltage generator 1101 or the receiver 1103 corresponding to the imaging channels numbered 64 to 80.

Figure 7:
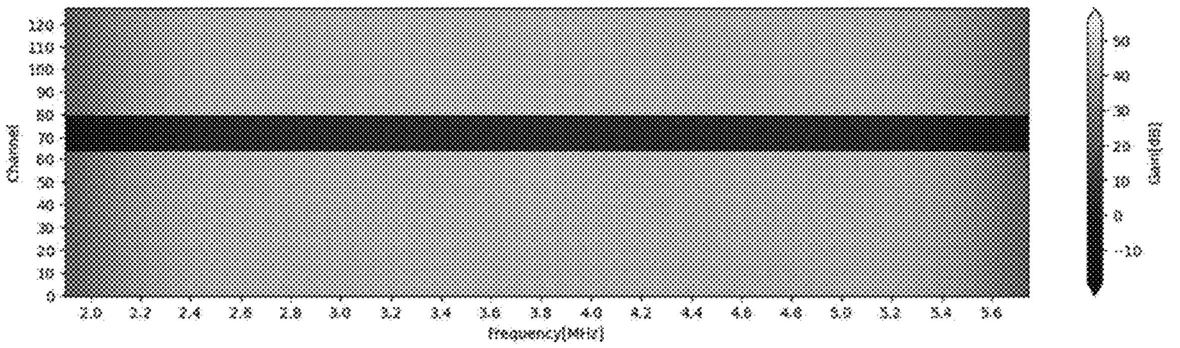
FIG. 7 is another schematic diagram of another representation of an energy pulse analysis result.

FIG. 7 is another schematic diagram of another representation of an energy pulse analysis result. In FIG. 7, the vertical axis represents identification information (e.g., a number) of each imaging channel of the front end portion 110, for example, the numbers of the imaging channels are from 0 to 127. The horizontal axis represents the frequency of a signal of each imaging channel in megahertz (MHz). Different grayscales or colors represent signal gains in decibels (dB).

FIG. 7 corresponds to FIG. 6, and in FIG. 7, signal gains of the imaging channels numbered 64 to 80 at each frequency are obviously lower than those of the other channels. Therefore, the control apparatus 12 determines that a fault has occurred in the voltage generator 1101 or the receiver 1103 corresponding to the imaging channels numbered 64 to 80.

Insofar as FIG. 6 corresponds to FIG. 7, the display apparatus 13 of the medical imaging system 1 may further display a state of each voltage generator 1101 and a state of each receiver 1103, thereby helping an operator or a maintenance person to further determine a fault location.

Figure 8:
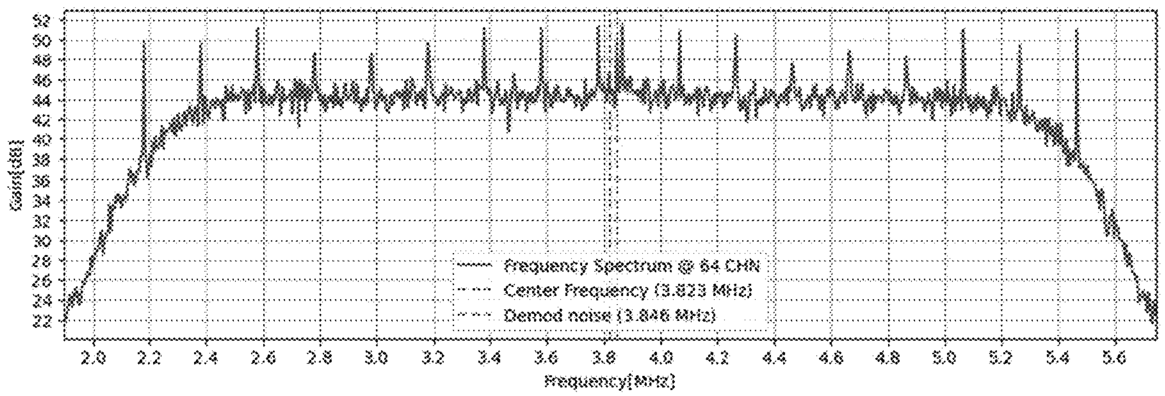
FIG. 8 is another schematic diagram of a frequency spectrum of an imaging channel obtained by a control apparatus 12 by performing frequency spectrum analysis on first data.

FIG. 8 is another schematic diagram of a frequency spectrum of an imaging channel obtained by a control apparatus 12 by performing frequency spectrum analysis on first data. FIG. 8 shows, for example, a frequency spectrum of the imaging channel 64.

In FIG. 8, a plurality of peaks 81 (some of the peaks 81 are shown in the figure) appear, corresponding to noise at a plurality of frequencies.

In the present application, if noise occurs at a plurality of frequencies of one imaging channel, the control apparatus 12 determines that the front end portion 110 is being interfered with by an external signal. Therefore, in the example shown in FIG. 8, the control apparatus 12 determines that the front end portion 110 is being interfered with by an external signal, and the interference affects a signal of the imaging channel 64.

Figure 9:
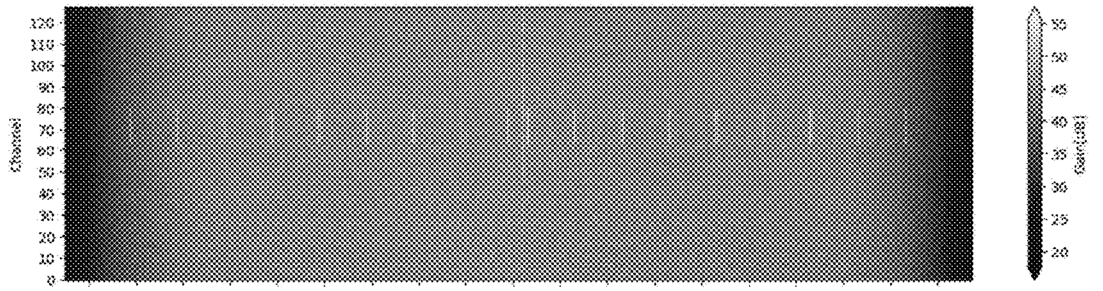
FIG. 9 is still another schematic diagram of an energy pulse analysis result.

FIG. 9 is still another schematic diagram of an energy pulse analysis result, corresponding to FIG. 8. As shown in FIG. 9, the signal gains of the imaging channels numbered 64 to 80 at some frequencies are obviously higher (e.g., corresponding to the gains of the peaks of FIG. 8) than those of the other channels. Therefore, the control apparatus 12 determines that the front end portion 110 is being interfered with by an external signal, and the interference affects the imaging channels numbered 64 to 80.

In the above, methods for detecting or determining different types of faults are described with reference to FIG. 4 to FIG. 9. It should be noted that the foregoing type of fault may not be singular, for example, there may be more than one type of fault. Therefore, the result of the frequency spectrum analysis or the result of the energy pulse analysis may be a combination of the foregoing cases.

As shown in FIG. 1, the control method for the medical imaging system may further include:

- operation 102: controlling a display apparatus 13 of a medical imaging system 1 to display at least one of the following pieces of information:
- information about an imaging channel corresponding to an element 1104 in which a fault has occurred in a probe 1102;
- information about an imaging channel corresponding to a voltage generator 1101 in which a fault has occurred;
- information about an imaging channel corresponding to a receiver 1103 in which a fault has occurred; and
- information about an imaging channel being interfered with by an external signal.

Therefore, the information related to the fault that has occurred in the front end portion 110 can be displayed in the display apparatus 13, and an operator or a maintenance person of the medical imaging system 1 can easily learn of the information related to the fault, to appropriately use the medical imaging system 1 or perform repairs.

In some examples: the imaging channel corresponding to the element 1104 in which a fault has occurred in the probe 1102 may be displayed in a highlighted manner. For example, the highlighted display includes: using a first color (e.g., green) to represent information about an imaging channel corresponding to an element 1104 in which no fault has occurred, and using a second color (e.g., red) to represent the information about the imaging channel corresponding to the element 1104 in which a fault has occurred. Information about an imaging channel may include information such as an identifier (ID) and/or a signal amplitude of the imaging channel, and the information about the imaging channel may be in at least one of a text form and an image form.

In some other examples: the information about the imaging channel corresponding to the voltage generator 1101 in which a fault has occurred may be displayed in a highlighted manner. For example, the highlighted display includes: using the first color (e.g., green) to represent information about an imaging channel corresponding to a voltage generator 1101 in which no fault has occurred, and using the second color (e.g., red) to represent the information about the imaging channel corresponding to the voltage generator 1101 in which a fault has occurred. Information about an imaging channel may include information such as an identifier (ID) and/or a signal amplitude of the imaging channel, and the information about the imaging channel may be in at least one of a text form and an image form.

In still some examples: the information about the imaging channel corresponding to the receiver 1103 in which a fault has occurred may be displayed in a highlighted manner. For example, the highlighted display includes: using the first color (e.g., green) to represent information about an imaging channel corresponding to a receiver 1103 in which no fault has occurred, and using the second color (e.g., red) to represent the information about the imaging channel corresponding to the receiver 1103 in which a fault has occurred. Information about an imaging channel may include information such as an identifier (ID) and/or a signal amplitude of the imaging channel, and the information about the imaging channel may be in at least one of a text form and an image form.

In yet some examples: the information about the imaging channel being interfered with by an external signal may be displayed in a highlighted manner. For example, the highlighted display includes: using the first color (e.g., green) to represent information about an imaging channel that is not being interfered with by an external signal, and using a third color (e.g., red) to represent the information about the imaging channel being interfered with by an external signal. Information about an imaging channel may include information such as an identifier (ID) and/or a signal amplitude of the imaging channel, and the information about the imaging channel may be in at least one of a text form and an image form.

As shown in FIG. 1, the control method for the medical imaging system may further include:

- operation 103: controlling the display apparatus 13 of the medical imaging system 1 to display information about the probe 1102 having the element 1104 in which a fault has occurred.

When the medical imaging system 1 is equipped with a plurality of probes 1102, one of the probes 1102 is activated, and if it is detected in operation 102 that there is an element 1104 in which a fault has occurred in the activated probe 1102, the display apparatus 13 may display information about this probe 1102. In some examples, the information about the probe 1102 having the element 1104 in which a fault has occurred may be displayed in a highlighted manner. For example, the highlighted display includes: using the first color (e.g., green) to represent information about an unactivated probe 1102 or information about a probe 1102 that does not have an element 1104 in which a fault has occurred, and using the second color (e.g., red) to represent the information about the probe 1102 having the element 1104 in which a fault has occurred. Information about a probe 1102 may include information such as an identifier (ID) or a model of the probe, and the information about the probe 1102 may be in at least one of a text form and an image form.

As shown in FIG. 1, the control method for the medical imaging system may further include:

- operation 104: performing compensation processing on the fault to generate a medical image according to the imaging data.

In some examples, the compensation processing in operation 104 includes at least one of the following processing 1, processing 2, and processing 3:

processing 1: adjusting a weight value of the imaging data in an imaging channel corresponding to the fault;

processing 2: discarding the imaging data in the imaging channel corresponding to the fault; and processing 3: adjusting a filter coefficient of the imaging channel corresponding to the fault.

For example, in processing 1, the weight value of the imaging data in the imaging channel corresponding to the fault may be reduced. Therefore, during generation of a medical image, imaging data in a normal imaging channel can be fully utilized to generate the medical image.

For another example, in processing 2, the imaging data in the imaging channel corresponding to the fault may be discarded. Therefore, during generation of a medical image, interference of the imaging data in the imaging channel corresponding to the fault can be avoided, and imaging data in a normal imaging channel can be fully utilized to generate the medical image.

For still another example, when the front end portion 110 is interfered with by an external signal, processing 3 may be utilized to adjust a filter coefficient of an imaging channel affected by the interference. Therefore, the interference of the external signal to the front end portion 110 may be eliminated as much as possible by means of filter processing, thereby improving the imaging quality of a medical image.

In operation 104, processing 1, processing 2, and processing 3 may be used alone, or in combination, for different types of faults of the front end portion 110, so as to generate a medical image.

In the present application, the operator of the medical imaging system 1 may click a predetermined icon (e.g., a "repair" icon) on a user interface or operate a predetermined key or button to perform operation 104. Alternatively, the operation is automatically implemented by the control apparatus of the medical imaging system 1.

By means of operation 104, when a fault occurs in the front end portion 110, the medical imaging system 1 is still able to generate a medical image by utilizing multi-channel characteristics of the front end portion 110, thereby greatly improving the convenience of use of the medical imaging system 1. Therefore, the medical imaging system 1 can still be appropriately used for imaging while waiting for the medical imaging system 1 to be repaired, improving the use efficiency of the medical imaging system 1 and thereby shortening the waiting time of hospitals and patients.

As shown in FIG. 1, the control method for the medical imaging system may further include:

operation 105: indicating a region corresponding to the fault on the medical image.

In operation 105, a region corresponding to the fault may be indicated on the medical image generated in operation 104. For example, the region corresponding to the fault on the medical image may be indicated by means of at least one of a text form and an icon form. As a result, it is possible to indicate to a user of the medical imaging system 1 the region corresponding to the fault on the medical image, so that the user can perform appropriate determinations and further operations on the region corresponding to the fault. For example, if relatively important diagnostic information appears in the region corresponding to the fault, the user can perform more detailed scanning using means such as changing a probe or adjusting the orientation of the probe, to avoid obtaining the diagnostic information according to the region corresponding to the fault.

In the present application, the control method for the medical imaging system 1 shown in FIG. 1 may be performed periodically or performed under a predetermined condition. For example, the control method may be performed daily, weekly, or the like. For another example, the control method may be performed each time the medical imaging system 1 is powered on, may be performed when the medical imaging system 1 is connected to a new probe 1102, or may be performed when the medical imaging system 1 changes an activated probe 1102.

The following describes the control method for the medical imaging system with reference to a specific instance.

The instance may be based on the following examples:

The quantity N of imaging channels of the front end portion 110 is equal to 128, wherein numbers of the imaging channels may be from 0 to 127;

starting from the imaging channel numbered 0, every n=16 imaging channels form a group, a quantity M of groups of the imaging channels is equal to 8, and numbers of the groups are from 0 to 7;

the front end portion 110 has eight voltage generators 1101, and each voltage generator 1101 corresponds to one group of imaging channels;

the probe 1102 may have a plurality of elements 1104, and each element 1104 may correspond to one or more imaging channels; and the front end portion 110 has eight receivers 1103, and each receiver 1103 corresponds to one group of imaging channels.

In the instance, each time the medical imaging system 1 is powered on, the scanning device 11 scans air by using an activated probe 1102 to obtain first data, and the control apparatus 12 analyzes the first data to detect whether a fault has occurred in the front end portion 110 of the scanning device 11 and a type of the fault.

A detection result of the control apparatus 12 may be displayed on the display apparatus 13.

Figure 10:
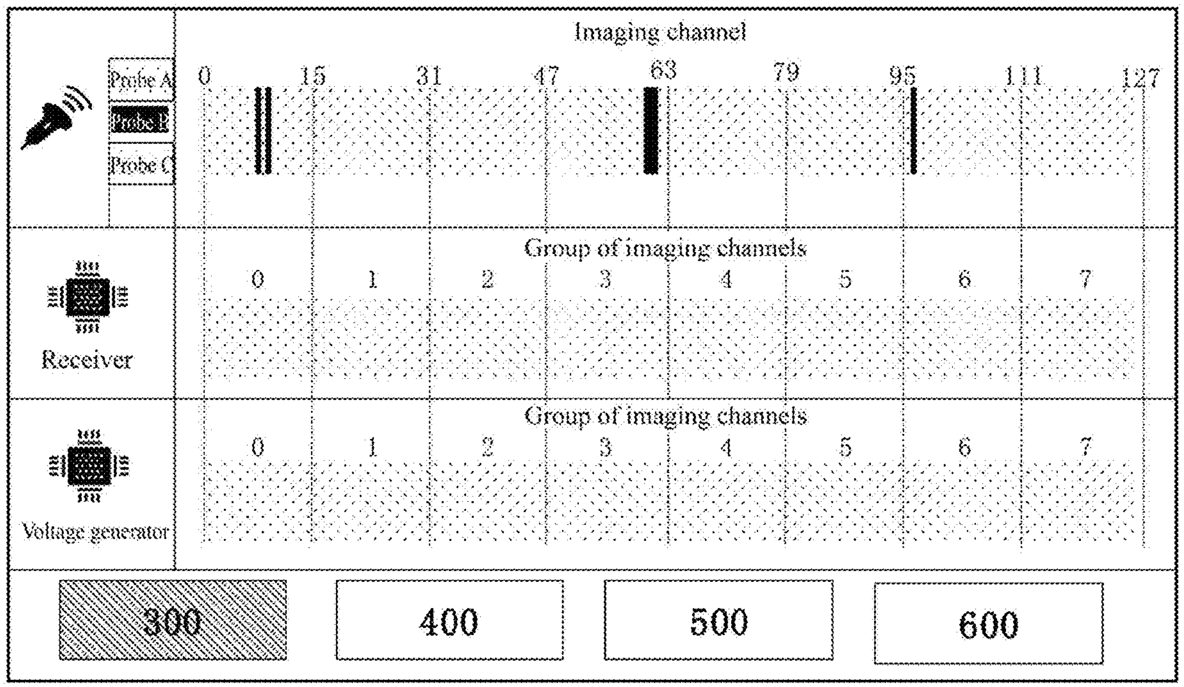
FIG. 10 is a schematic diagram of a picture that is displayed by a display apparatus 13 and that is used for reflecting a detection result.

FIG. 10 is a schematic diagram of a picture that is displayed by a display apparatus 13 and that is used for reflecting a detection result, which displays a picture after an icon 300 is pressed. The icon 300 may, for example, represent an overview of the detection result.

In the example shown in FIG. 10, the medical imaging system 1 is equipped with three probes, i.e., probe A, probe B, and probe C. Probe A and probe C are not faulty or are not activated, probe B is activated, and a fault has occurred in some elements in probe B. Probe A and probe C may be marked using the first color (e.g., green), and are displayed as dotted pattern-filled regions in FIG. 10. Probe B may be marked using the second color (e.g., red), and is displayed as a black-filled region in FIG. 10.

An imaging channel corresponding to an element in which no fault has occurred in probe B may be marked using the first color (e.g., green), and is displayed as a dotted pattern-filled region in FIG. 10, and an imaging channel corresponding to an element in which a fault has occurred may be marked using the second color (e.g., red), and is displayed as a black-filled region in FIG. 10.

In the example shown in FIG. 10, no fault has occurred in the receivers and the voltage generators. Therefore, groups of imaging channels corresponding to the receivers and the voltage generators are marked using the first color (e.g., green), and are displayed as dotted pattern-filled regions in FIG. 10.

Figure 11:
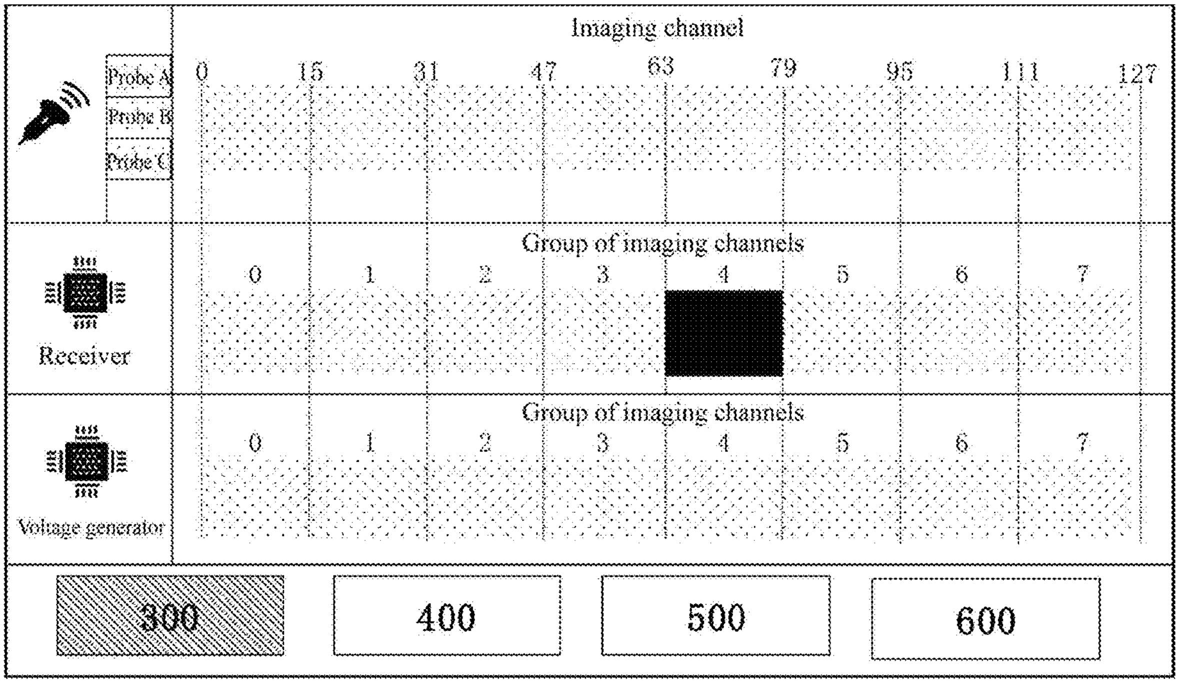
FIG. 11 is another schematic diagram of a picture that is displayed by a display apparatus 13 and that is used for reflecting a detection result.

FIG. 11 is another schematic diagram of a picture that is displayed by a display apparatus 13 and that is used for reflecting a detection result, which displays a picture after an icon 300 is pressed. The icon 300 may, for example, represent an overview of the detection result.

In the example shown in FIG. 11, a fault has occurred in one receiver, and imaging channels corresponding to the receiver in which the fault has occurred may be, for example, imaging channels included in group 4 of imaging channels, may be marked using the second color (e.g., red), and are displayed as a black-filled region in FIG. 11.

In the example shown in FIG. 11, each element of an activated probe (e.g., probe B) is normal, and each voltage generator is also normal. Therefore, an imaging channel corresponding to each element of the activated probe and a group of imaging channels corresponding to each voltage generator are marked using the first color (e.g., green), and are displayed as dotted pattern-filled regions in FIG. 11.

Figure 12:
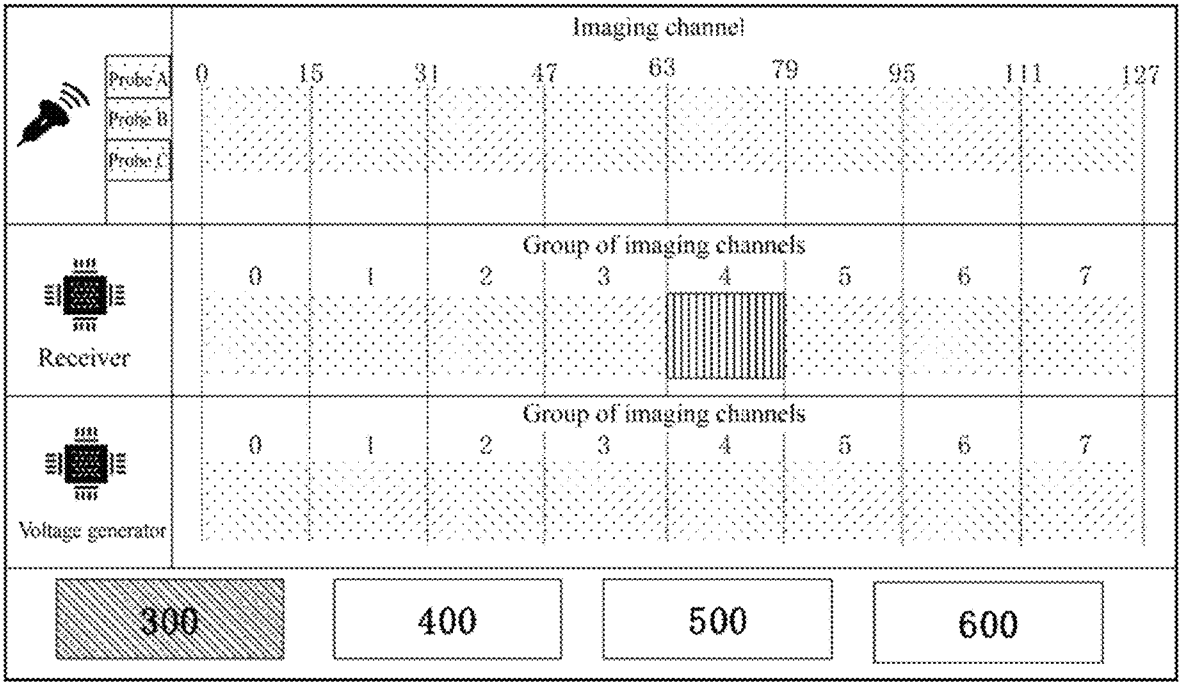
FIG. 12 is still another schematic diagram of a picture that is displayed by a display apparatus 13 and that is used for reflecting a detection result.

FIG. 12 is still another schematic diagram of a picture that is displayed by a display apparatus 13 and that is used for reflecting a detection result, which displays a picture after an icon 300 is pressed. The icon 300 may, for example, represent an overview of the detection result.

In the example shown in FIG. 12, the front end portion is interfered with by an external signal, and an imaging channels that are being interfered with may be, for example, imaging channels included in group 4 of imaging channels. Therefore, among groups of imaging channels corresponding to receivers, the imaging channels are marked using the third color (e.g., yellow), are displayed as a vertical stripe-filled region in FIG. 12, and may be displayed. Other groups of imaging channels corresponding to the receivers are marked using the first color (e.g., green), and are displayed as dotted pattern-filled regions in FIG. 12.

In the example shown in FIG. 12, each element of an activated probe (e.g., probe B) is normal, and each voltage generator is also normal. Therefore, an imaging channel corresponding to each element of the activated probe and a group of imaging channels corresponding to each voltage generator are marked using the first color (e.g., green), and are displayed as dotted pattern-filled regions in FIG. 12.

As shown in FIG. 10, FIG. 11, and FIG. 12, the picture that is displayed by the display apparatus 13 and that is used for reflecting the detection result may further include an icon 400. The icon 400 may represent an analysis. For example, the operator clicks the icon 400, and then at least one of the result of frequency spectrum analysis and the result of energy pulse analysis performed on the first data may be displayed in the picture. For example, corresponding to the case of FIG. 10, the operator clicks the icon 400, and then at least one of FIG. 4 and FIG. 5 may be displayed in the picture, corresponding to the case of FIG. 11, the operator clicks the icon 400, and then at least one of FIG. 6 and FIG. 7 may be displayed in the picture, and corresponding to the case of FIG. 12, the operator clicks the icon 400, and then at least one of FIG. 8 and FIG. 9 may be displayed in the picture.

As shown in FIG. 10, FIG. 11, and FIG. 12, the picture that is displayed by the display apparatus 13 and that is used for reflecting the detection result may further include an icon 500. The icon 500 may represent repair. For example, the operator clicks the icon 500, and then the control apparatus 12 may perform operation 104, to generate a medical image according to imaging data.

Figure 13:
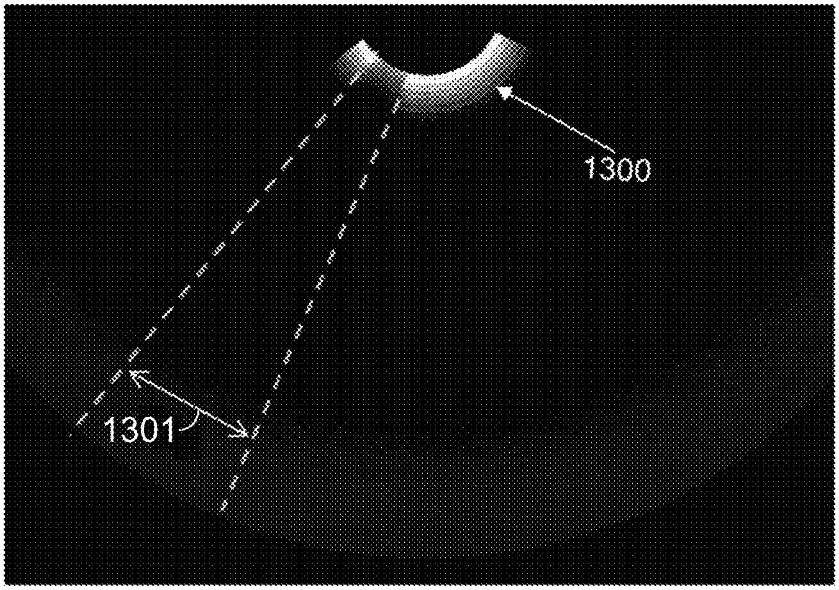
FIG. 13 is a schematic diagram of a medical image generated based on operation 104.

FIG. 13 is a schematic diagram of a medical image generated based on operation 104. As shown in FIG. 13, the display apparatus 13 displays the medical image 1300. In addition, the display apparatus 13 also marks a region 1301 corresponding to a fault on the medical image 1300. The region 1301 corresponding to the fault is, for example, generated by using imaging data in an imaging channel corresponding to the fault.

As shown in FIG. 10, FIG. 11, and FIG. 12, the picture that is displayed by the display apparatus 13 and that is used for reflecting the detection result may further include an icon 600. The icon 600 may represent a service. For example, the operator may click the icon 600, and then an analysis result of the control apparatus 12 may be sent to a server. Therefore, a device or a person of the server may perform further analysis or provide a repair suggestion, a service, or the like.

According to the embodiments of the present application, the operator of the medical imaging system can determine the availability of the medical imaging system according to the type of the fault. Therefore, the medical imaging system is appropriately used while waiting for the medical imaging system to be repaired, so as to improve the stability of the medical imaging system. In addition, the operator can continue to use the medical imaging system to generate a medical image when a fault has occurred in a front end of the scanning device, thereby reducing the waiting time of a user.

The following describes operating principles of an ultrasound imaging system used as a medical imaging system in the present application.

Figure 14:
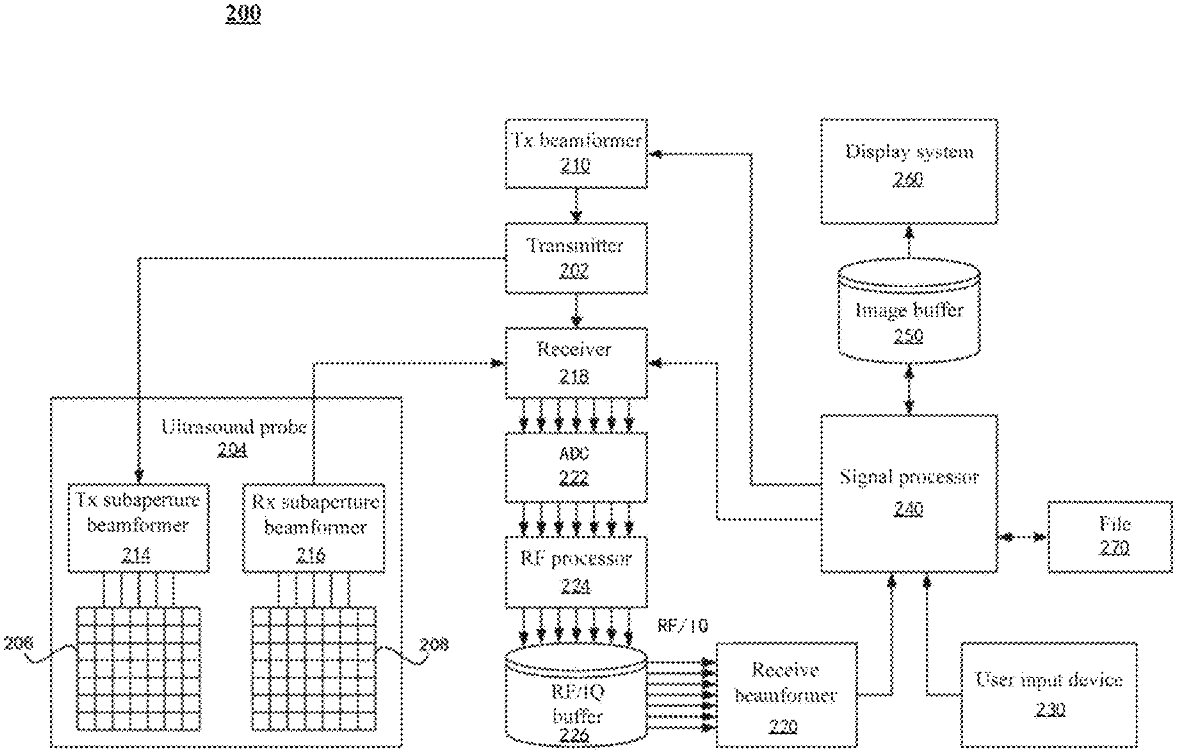
FIG. 14 is a schematic diagram of an ultrasound imaging system according to embodiments of the present application.

FIG. 14 is a schematic diagram of an ultrasound imaging system according to embodiments of the present application. As shown in FIG. 14, the ultrasound imaging system 200 may be configured to provide ultrasound imaging, and may therefore include suitable circuitry, interfaces, logic, and/or code for performing and/or supporting ultrasound imaging-related functions. The ultrasound imaging system 200 may correspond to the medical imaging system 1 of FIG. 2.

The ultrasound imaging system 200 includes, for example, a transmitter 202, an ultrasound probe 204 (corresponding to the foregoing scanning device 11), a transmit beamformer 210, a receiver 218, a receive beamformer 220, an RF processor 224, an RF/IQ buffer 226, a user input module 230, a signal processor 240 (corresponding to the foregoing control apparatus 12), an image buffer 250, a display system 260 (including the foregoing display apparatus 13), and a file 270.

The transmitter 202 may include suitable circuitry, interfaces, logic, and/or code operable to drive the ultrasound probe 204. The ultrasound probe 204 (corresponding to the foregoing probe 1102) may include a two-dimensional (2D) piezoelectric element (corresponding to the foregoing element 1104) array. The ultrasound probe 204 may include a set of transmitting transducer elements 206 and a set of receiving transducer elements 208 that typically form the same element. In some embodiments, the ultrasound probe 204 is operable to acquire ultrasound image data covering at least a substantial portion of an anatomical structure (such as the heart or any suitable anatomical structure).

The transmit beamformer 210 may include suitable circuitry, interfaces, logic, and/or code that is operable to control the transmitter 202, and the transmitter 202 drives the set of transmitting transducer elements 206 by means of a transmit subaperture beamformer 214 to transmit an ultrasound emission signal into a region of interest (e.g., a person, animal, subsurface cavity, physical structure, etc.). The emitted ultrasound signal can be backscattered from structures in an object of interest (e.g., blood cells or tissue) to produce an echo. The echo is received by the receiving transducer element 208.

The set of receiving transducer elements 208 in the ultrasound probe 204 is operable to convert the received echo to an analog signal for subaperture beam formation through a receiving subaperture beamformer 216, which is then transmitted to the receiver 218. The receiver 218 may include suitable circuitry, interfaces, logic, and/or code that is operable to receive signals from the receiving subaperture beamformer 216. The analog signal can be transferred to one or more of a plurality of A/D converters 222.

The plurality of A/D converters 222 may include suitable circuitry, interfaces, logic, and/or code that is operable to convert the analog signal from the receiver 218 to a corresponding digital signal. The plurality of A/D converters 222 are provided between the receiver 218 and the RF processor 224. Nevertheless, the present application is not limited in this regard. Thus, in some embodiments, the plurality of A/D converters 222 may be integrated within the receiver 218.

The RF processor 224 may include suitable circuitry, interfaces, logic, and/or code that is operable to demodulate the digital signals output by the plurality of A/D converters 222. According to one embodiment, the RF processor 224 may include a complex demodulator (not shown) that is operable to demodulate the digital signal to form an I/Q data pair representing the corresponding echo signal. The RF or I/Q signal data can then be transferred to the RF/IQ buffer 226. The RF/IQ buffer 226 may include suitable circuitry, interfaces, logic, and/or code that is operable to provide temporary storage of RF or I/Q signal data generated by the RF processor 224.

The receive beamformer 220 may include suitable circuitry, interfaces, logic, and/or code that may be operable to perform digital beamforming processing to, for example, sum and output a beam summing signal for the delay-channel signals received from the RF processor 224 via the RF/IQ buffer 226. The resulting processed information may be the beam summing signal outputted from the receive beamformer 220 and transmitted to the signal processor 240. According to some embodiments, the receiver 218, the plurality of A/D converters 222, the RF processor 224, and the beamformer 220 may be integrated into a single beamformer which may be digital. In various embodiments, the ultrasound imaging system 200 includes a plurality of receive beamformers 220.

The user input device 230 can be used to enter patient data, scan parameters, and settings, and select protocols and/or templates to interact with the AI segmentation processor, so as to select tracking targets, etc. In an illustrative embodiment, the user input device 230 is operable to configure, manage, and/or control the operation of one or more components and/or modules in the ultrasound imaging system 200. In this regard, the user input device 230 is operable to configure, manage, and/or control the operation of the transmitter 202, the ultrasound probe 204, the transmit beamformer 210, the receiver 218, the receive beamformer 220, the RF processor 224, the RF/IQ buffer 226, the user input device 230, the signal processor 240, the image buffer 250, the display system 260, and/or the file 270.

For example, the user input devices 230 may include buttons, rotary encoders, touch screens, motion tracking, voice recognition, mouse devices, keyboards, trackballs, cameras, and/or any other devices capable of receiving user commands. In some embodiments, for example, one or more of the user input devices 230 may be integrated into other components (such as the display system 260 or the ultrasound probe 204). As an example, the user input device 230 may include a touch screen display. As another example, the user input device 230 may include an accelerometer, gyroscope, and/or magnetometer attached to and/or integrated with the probe 204 to provide pose and motion recognition of the probe 204, such as identifying one or more probe compressions against the patient's body, predefined probe movements, or tilt operations, etc. Additionally and/or alternatively, the user input device 230 may include image analysis processing to identify the probe pose by analyzing the captured image data.

The signal processor 240 may include suitable circuitry, interfaces, logic, and/or code that is operable to process the ultrasound scan data (i.e., summed IQ signals) to generate an ultrasound image for presentation on the display system 260. The signal processor 240 is operable to perform one or more processing operations based on a plurality of selectable ultrasound modalities on the acquired ultrasound scan data. In an illustrative embodiment, the signal processor 240 is operable to perform display processing and/or control processing, etc. As the echo signal is received, the acquired ultrasound scan data can be processed in real-time during the scan session. Additionally or alternatively, the ultrasound scan data may be temporarily stored in the RF/IQ buffer 226 during the scan session and processed in a less real-time manner during online or offline operation. In various embodiments, the processed image data may be presented at the display system 260 and/or may be stored in the file 270. The file 270 can be a local file, a picture archiving and communication system (PACS), or any suitable device for storing images and related information.

The signal processor 240 may be one or more central processing units, microprocessors, microcontrollers, etc. For example, the signal processor 240 may be an integrated component, or may be distributed in various locations. The signal processor 240 may be configured to receive input information from the user input device 230 and/or file 270, generate outputs that may be shown by the display system 260, and manipulate the outputs, etc., in response to the input information from the user input device 230. The signal processor 240 may be capable of executing, for example, any of one or more of the methods and/or one or more sets of instructions discussed herein according to various embodiments.

The ultrasound imaging system 200 may be operated to continuously acquire ultrasound scan data at a frame rate suitable for the imaging situation under consideration. Typical frame rates are in the range of 20 to 220, but can be lower or higher. The acquired ultrasound scan data can be shown on the display system 260 in real-time at a display rate that is the same as the frame rate, or slower, or faster than the frame rate. The image buffer 250 is included to store frames for processing of the acquired ultrasound scan data that are not scheduled for immediate display. Preferably, the image buffer 250 has sufficient capacity to store frames of ultrasound scan data for at least a few minutes. Frames of ultrasound scan data are stored in such a way that they can be easily retrieved therefrom according to their acquisition sequence or time. The image buffer 250 may be embodied in any known data storage medium.

In some specific embodiments, the signal processor 240 may be configured to perform or otherwise control at least some of the functions performed thereby based on user instructions via the user input device 230. As an example, the user may provide voice commands, probe poses, button presses, etc. to issue specific commands such as controlling aspects of automatic strain measurement and strain ratio calculations, and/or provide or otherwise specify various parameters or settings associated therewith, as described in more detail below.

During operation, the ultrasound imaging system 200 may be used to generate ultrasound images, including two-dimensional (2D), three-dimensional (3D), and/or four-dimensional (4D) images. In this regard, the ultrasound imaging system 200 is operable to continuously acquire ultrasound scan data at a specific frame rate, which may be applicable to the imaging situation discussed. For example, the frame rate can be in the range of 20-70, or can be lower or higher. The acquired ultrasound scan data can be shown on the display system 260 at the same display rate as the frame rate, or slower, or faster than the frame rate. The image buffer 250 is included to store frames for processing of the acquired ultrasound scan data that are not scheduled for immediate display. Preferably, the image buffer 250 has sufficient capacity to store at least a few seconds of frames of ultrasound scan data. Frames of ultrasound scan data are stored in such a way that they can be easily retrieved therefrom according to their acquisition sequence or time. The image buffer 250 may be embodied in any known data storage medium.

In some cases, the ultrasound imaging system 200 may be configured to support grayscale and color-based operations. For example, the signal processor 240 may operate to perform grayscale B-model processing and/or color processing. Grayscale B-model processing may include processing B-model RF signal data or IQ data pairs. For example, the grayscale B-model processing can enable the formation of an envelope of the received beam summing signal by computing the amount $(I^2+Q^2)^{1/2}$. The envelope can be subjected to additional B-model processing, such as logarithmic compression to form the display data. The display data can be converted to X-Y format for video display. Scan-converted frames can be mapped to grayscale for display. The B model frame is provided to the image buffer 250 and/or the display system 260. Color processing may include processing color-based RF signal data or IQ data pairs to form frames to cover the B-model frames being provided to image buffer 250 and/or display system 260. Grayscale and/or color processing may be adaptively adjusted based on user input (e.g., selections from the user input device 230), such as for enhancing the grayscale and/or color of a particular region.

The embodiments of the present application further provide a computer-readable program, wherein the program, when executed, causes a computer to perform, in a medical imaging system, the control method described in any of the foregoing embodiments.

The embodiments of the present application further provide a storage medium storing a computer-readable program, wherein the computer-readable program causes a computer to perform, in a medical imaging system, the control method described in any of the foregoing embodiments.

A non-transitory computer-readable medium has a computer program stored thereon, wherein the computer program has at least one code segment, and the at least one code segment is executable by a machine to cause the machine to perform the control method described in any of the foregoing embodiments.

The above embodiments merely provide illustrative descriptions of the embodiments of the present application. However, the present application is not limited thereto, and appropriate variations may be made on the basis of the above embodiments. For example, each of the embodiments described above may be used independently, or one or more among the above embodiments may be combined.

The present application is described above with reference to specific embodiments. However, it should be clear to those skilled in the art that the foregoing description is merely illustrative and is not intended to limit the scope of protection of the present application. Various variations and modifications may be made by those skilled in the art according to the spirit and principle of the present application, and these variations and modifications also fall within the scope of the present application.

Preferred embodiments of the present application are described above with reference to the accompanying drawings. Many features and advantages of the embodiments are clear according to the detailed description. Therefore, the appended claims are intended to cover all these features and advantages that fall within the true spirit and scope of these embodiments. In addition, as many modifications and changes could be easily conceived of by those skilled in the art, the embodiments of the present application are not limited to the illustrated and described precise structures and operations, but can encompass all appropriate modifications, changes, and equivalents that fall within the scope of the embodiments.

The invention claimed is:

1. A method for controlling an ultrasound imaging system, the ultrasound imaging system comprising a scanning device, configured to scan an object to be tested, to obtain imaging data containing information about the object to be tested, wherein the scanning device has a front end portion for transmitting a signal to and receiving a signal from the object to be tested, wherein the front end portion comprises a plurality of elements divided into a plurality of groups each comprising multiple elements, and wherein each group communicates through a respective imaging channel, the method comprising:

detecting, according to data obtained by the scanning device by scanning a predetermined object to be tested, a type of a fault that has occurred in the front end portion of the scanning device and an imaging channel corresponding to the fault; and performing channel-level compensation processing on the imaging channel corresponding to the fault to generate a medical image according to the imaging data.

2. The method for controlling the ultrasound imaging system according to claim 1, wherein the front end portion comprises:

a voltage generator, the voltage generator generating a pulse voltage;

a probe, the probe having the plurality of elements, and the elements transmitting signals or receiving signals under the driving of the pulse voltage; and a receiver, the receiver processing electrical signals corresponding to the signals received by the elements.

3. The method for controlling the ultrasound imaging system according to claim 2, wherein the type of the fault that has occurred in the front end portion comprises at least one of:

a fault that has occurred in at least one element of the probe;

a fault that has occurred in the voltage generator;

a fault that has occurred in the receiver; and interference to the front end portion caused by an external signal.

4. The method for controlling the ultrasound imaging system according to claim 3, wherein the method further comprises:

controlling a display apparatus of the medical imaging system to display at least one of the following pieces of information:

information about the imaging channel corresponding to the element in which the fault has occurred in the probe;

information about the imaging channel corresponding to the voltage generator in which the fault has occurred;

information about the imaging channel corresponding to the receiver in which the fault has occurred; and information about the imaging channel being interfered with by an external signal.

5. The method for controlling the ultrasound imaging system according to claim 2, wherein the quantity of probes is one or more; and the control method further comprises:

controlling a display apparatus of the medical imaging system to display information about the probe having an element in which the fault has occurred.

6. The method for controlling the ultrasound imaging system according to claim 1, wherein the channel-level compensation processing comprises at least one of the following:

adjusting a weight value of the imaging data in an imaging channel corresponding to the fault;

discarding the imaging data in the imaging channel corresponding to the fault; and adjusting a filter coefficient of the imaging channel corresponding to the fault.

7. The method for controlling the ultrasound imaging system according to claim 1, wherein the control method further comprises:

indicating a region corresponding to the fault on the medical image.

8. The method for controlling the ultrasound imaging system according to claim 1, wherein the predetermined object to be tested is air.

9. The method for controlling the ultrasound imaging system according to claim 1, wherein the detecting, according to data obtained by the scanning device by scanning a predetermined object to be tested, the type of the fault that has occurred in the front end portion of the scanning device comprises:

performing at least one of frequency spectrum analysis and energy pulse analysis on the data obtained by the scanning device by scanning the predetermined object to be tested; and determining, according to a result of the analysis, the type of the fault that has occurred in the front end portion of the scanning device.

10. The method according to claim 1, wherein a quantity of imaging channels is the same as a quantity of the groups.

11. An ultrasound imaging system, comprising:

a scanning device, configured to scan an object to be tested, to obtain imaging data containing information about the object to be tested, wherein the scanning device has a front end portion for transmitting a signal to and receiving a signal from the object to be tested, wherein the front end portion comprises a plurality of elements divided into a plurality of groups each comprising multiple elements, and wherein each group communicates through a respective imaging channel;

a memory storing instructions; and a processor configured to execute the instructions to:

detect, according to data obtained by the scanning device by scanning a predetermined object to be tested, a type of a fault that has occurred in the front end portion of the scanning device and an imaging channel corresponding to the fault; and perform channel-level compensation processing on the imaging channel corresponding to the fault to generate a medical image according to the imaging data.

12. The system according to claim 11, wherein a quantity of imaging channels is the same as a quantity of the groups.

13. The system according to claim 12, wherein the front end portion comprises:

a voltage generator, the voltage generator generating a pulse voltage;

a probe, the probe having the plurality of elements, and the elements transmitting signals or receiving signals under the driving of the pulse voltage; and a receiver, the receiver processing electrical signals corresponding to the signals received by the elements.

14. The system according to claim 13, wherein the type of the fault that has occurred in the front end portion comprises at least one of:

a fault that has occurred in at least one element of the probe;

a fault that has occurred in the voltage generator;

a fault that has occurred in the receiver; and interference to the front end portion caused by an external signal.

15. The system according to claim 14, wherein the processor is further configured to:

control a display apparatus of the medical imaging system to display at least one of the following pieces of information:

information about the imaging channel corresponding to the element in which the fault has occurred in the probe;

information about the imaging channel corresponding to the voltage generator in which the fault has occurred;

information about the imaging channel corresponding to the receiver in which the fault has occurred; and information about the imaging channel being interfered with by an external signal.

16. The system according to claim 13, wherein the quantity of probes is one or more; and the processor is further configured to:

control a display apparatus of the ultrasound imaging system to display information about the probe having an element in which a fault has occurred.

17. The system according to claim 11, wherein the channel-level compensation processing comprises at least one of the following:

adjusting a weight value of the imaging data in the imaging channel corresponding to the fault;

discarding the imaging data in the imaging channel corresponding to the fault; and adjusting a filter coefficient of the imaging channel corresponding to the fault.

18. The system according to claim 11, wherein the processor is further configured to:

indicate a region corresponding to the fault on the medical image.

19. The system according to claim 11, wherein the predetermined object to be tested is air.

20. A non-transitory computer-readable medium, having a computer program stored therein, wherein the computer program has at least one code segment, the at least one code segment being executable by a machine to cause the machine to:

detect, according to data obtained by scanning a predetermined object to be tested with a scanning device, a type of a fault that has occurred in a front end portion of the scanning device and an imaging channel corresponding to the fault; and perform channel-level compensation processing on the imaging channel corresponding to the fault to generate a medical image according to the imaging data, wherein the machine has a front end portion for transmitting a signal to and receiving a signal from the object to be tested, wherein the front end portion comprises a plurality of elements divided into a plurality of groups each comprising multiple elements, and wherein each group communicates through a respective imaging channel.

* * * * *